US006312149B1

(12) United States Patent
Sjövall et al.

(10) Patent No.: US 6,312,149 B1
(45) Date of Patent: Nov. 6, 2001

(54) MIXING DEVICE

(75) Inventors: Peter Åke Sjövall, Södra Sandby; Lars Åke Alvar Lidgren, Lund, both of (SE)

(73) Assignee: Scandimed International AB, Sjobo (SE)

( * ) Notice: Subject to any disclaimer, the term of this patent is extended or adjusted under 35 U.S.C. 154(b) by 0 days.

(21) Appl. No.: 09/507,243

(22) Filed: Feb. 18, 2000

(30) Foreign Application Priority Data

Feb. 26, 1999 (SE) .................................................. 9900688

(51) Int. Cl.$^7$ ...................................................... B01F 11/00
(52) U.S. Cl. ...................... 366/130; 366/139; 366/189; 366/256; 366/332
(58) Field of Search ........................ 366/139, 130, 366/189, 163.1, 256, 267, 262, 332, 333

(56) References Cited

U.S. PATENT DOCUMENTS

| Re. 35,276 | 6/1996 | Chan ........................ 366/139 |
| 4,469,153 | * 9/1984 | Morrisette . |
| 5,435,645 | 7/1995 | Faccioli et al. .................. 366/139 |
| 5,501,520 | 3/1996 | Lidgren et al. .................. 366/139 |
| 5,549,380 | 8/1996 | Lidgren et al. .................. 366/139 |
| 5,551,778 | 9/1996 | Hauke et al. ................... 366/139 |
| 5,588,745 | 12/1996 | Tanaka et al. .................. 366/139 |
| 5,779,356 | 7/1998 | Chan ........................ 366/139 |
| 5,797,678 | * 8/1998 | Murray ...................... 366/139 |
| 5,934,803 | * 8/1999 | Hutter ....................... 366/139 |
| 6,024,480 | * 2/2000 | Seaton et al. .................. 366/139 |
| 6,042,262 | * 3/2000 | Hajianpour ................... 366/139 |
| 6,116,773 | * 9/2000 | Murray ...................... 366/139 |

FOREIGN PATENT DOCUMENTS

| 2921565 | 12/1980 | (DE) . |
| 19532015 | 3/1997 | (DE) . |
| 500430 | 6/1994 | (SE) . |
| WO-93/22041 | * 11/1993 | (WO) . |
| WO-94/264403 | * 11/1994 | (WO) . |
| WO-95/00240 | * 1/1995 | (WO) . |
| WO9718031 | 5/1997 | (WO) . |

OTHER PUBLICATIONS

WIPO Abstract WO 94/26403 Nov. 24, 1994, One Sheet.

WIPO Abstract WO 97/18031 May 22, 1997, One Sheet.

* cited by examiner

Primary Examiner—Tony G. Soohoo
(74) Attorney, Agent, or Firm—Tarolli, Sundheim, Covell, Tummino & Szabo L.L.P.

(57) ABSTRACT

The present invention relates to a mixing device for the manufacture of bone cement by mixing components intended therefor, said mixing device including a mixing member (1) with a mixing space (2) for mixing of said components (11, 12). A vacuum-generating device (17) is provided to generate a vacuum in the mixing space (2) for mixing said components (11, 12) under vacuum. A mixing means (10) is provided to mix the components (11, 12) with each other in the mixing space (2). A sealed container (20) with one of the components (12) is provided in an outer container (22). The sealed container (20) can be opened when it is provided in the outer container (22) to permit flow of one of the components (12) to the other component (11) in the mixing space (2) for mixing of said components (11, 12). The outer container (22) and an end portion (5 or 3) of the mixing member (1) can be connected to each other and the mixing means (10) is movably mounted relative to the mixing space (2) at an opposite end portion (3 or 5) of the mixing member (1).

37 Claims, 5 Drawing Sheets

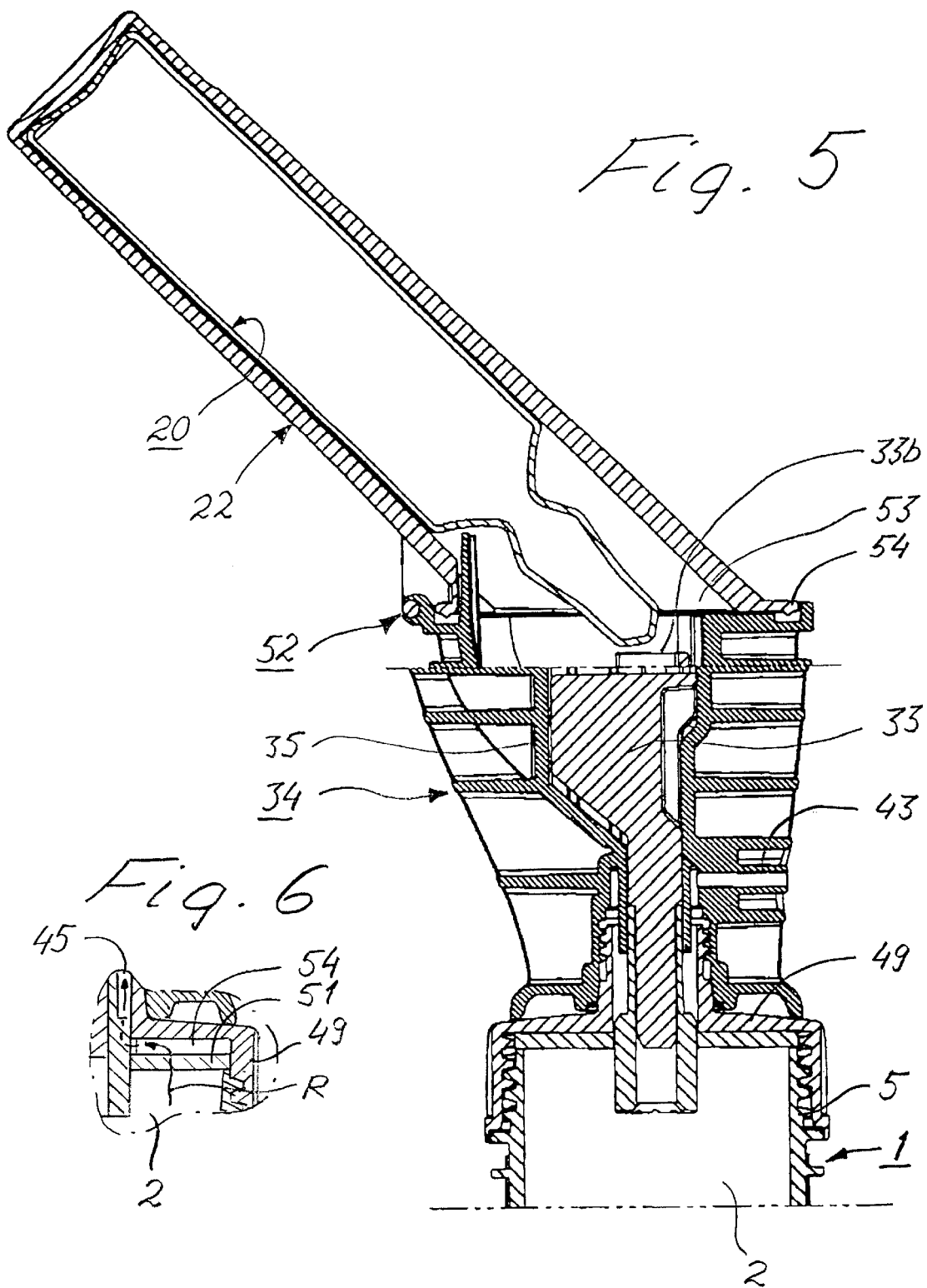

MIXING DEVICE

TECHNICAL FIELD

The present invention relates to a mixing device for the manufacture of bone cement.

BACKGROUND OF THE INVENTION

Devices for mixing of bone cement must meet a plurality of high requirements. Mixing and application of bone cement are critical moments in many common operations such as joint surgery, neurosurgery and dental surgery, and it is therefore of utmost importance that the mixing equipment is designed as user friendly and safe as possible. The technique for carrying through mixing and the way the cement is applied in the body, drastically affects the quality of the hardened or set bone cement and thus, the term of life of e.g., the hip or knee implant. In the leading mixing systems of today, mixing is therefore conducted under a vacuum, which reduces the porosity and thus, increases the fatigue strength of the hardened or set cement, and the mixed cement is discharged by means of a discharge gun directly from the mixing container, through a tip mounted thereon, to the desired location in the body, e.g., the thigh bone for fixing the hip implant.

Most mixing devices used today require that the person mixing the bone cement, the surgeon or the sterile nurse, themselves open the packages for the cement components, usually a bag for the powder component and a glass ampoule or vial for the liquid component, and pour these into the mixing container. This moment has several risks.

First, there is a risk that the nurse when breaking the ampoule or vial spills liquid and/or cuts herself on the sharp edges formed on the surfaces of fracture of the glass ampoule or vial. Another problem is that the operating personell is subjected to irritating and eventually harmful vapours which are set free from the liquid component in connection with the opening of the ampoule or vial and the transfer to the mixing container. In order to eliminate these problems, several mixing devices have been proposed, see e.g. U.S. Pat. Nos. 5,549,380, 5,551,778, 5,779,356, U.S. Pat. No. Re 35 276 and U.S. Pat. No. 5,588,745, wherein the cement components are transferred to the mixing container without exposing any component to the surrounding air, i.e. in a completely sealed system. Before mixing in said devices, the powder component is kept in the mixing space, while the liquid component is kept either beside or in direct connection with the mixing container in a package adapted particularly therefor. The demand for a specialized package for the liquid component however, causes substantial practical problems. The liquid component requires special pouring into the package particularly adapted therefor, which is a substantial problem of the manufacturing technique since aseptic filling must be practised. Furthermore, the mixing system is limited to mixing of those types of cement which are available in the special packages belonging to the mixing system.

The present invention avoids the above problems since the mixing device makes possible a completely sealed mixing of bone cement with bone cement components packed up in standard packings, i.e. liquid component in a glass ampoule or vial and powder component in a bag. Before mixing, the glass ampoule or vial is placed in a separate outer container which is connected to the mixing container, which contains the powder component. After the sealed system, consisting of container for liquid component and mixing container, has been evacuated by means of a vacuum source, the tip of the glass ampoule or vial is broken off, whereby the liquid component flows into the mixing container and comes in contact with the powder component, thereby initiating the mixing procedure. Since the container is easily modified for differently sized glass ampoules or vials, the device may be used for mixing of all common cement types on the market.

The publication U.S. Pat. No. 5,435,645 relates to a mixing device at which a sealed container—a container with a monomer component—is located in an outer container. The mixing member of the mixing device has a space to which the outer container is adapted and into which said outer container is screwed. Such a construction of the mixing device necessitates manufacture of a special type of monomer container since this container must fit into the outer container which in turn must fit into the mixing member. Furthermore, this mixing device has no mixing means which is provided in the mixing space of the mixing member for advantageous mixing.

The publications WO 97/18031 and SE 500 430 relate to mixing devices at which the outer containers with the sealed containers may be connected to a tubular mixing means and when the sealed containers are opened, the component therein is fed through the tubular mixing means to the mixing space and the component provided therein. Such an embodiment requires a special type of tubular mixing means which must be sealed by means of sealing rods such that air can not flow into the mixing device during mixing. At an embodiment according to the publication WO 97/18031 the outer container is through a hose connected to the side of the mixing member and thus, requires making a hole in the side of the mixing member through which air can flow into the mixing space and/or components flow out of said mixing space when the hose is released.

Since the mixing device according to the invention has the abovementioned characterizing features, harmful exposure to the vapours of the liquid component and other risks are eliminated, it becomes possible to use an outer container for different existing monomer containers at one and same mixing member, mixing may occur under a vacuum and by means of a mixing means provided in the mixing space of the mixing member and there is no risk for penetration of air into the mixing device after bringing together the two components and until mixing is complete.

SUMMARY OF THE INVENTION

The present invention relates to a mixing device for the manufacture of bone cement by mixing components intended therefore, said mixing device including a mixing member with a mixing space for mixing of said components, wherein the components are provided separated from each other before mixing thereof in the mixing device, wherein a first component for the manufacture of bone cement is provided in the mixing space in which mixing is to be carried through, wherein a second component for the manufacture of bone cement is provided in at least one sealed container, wherein an opening device is provided for opening the sealed container, wherein a vacuum-generating device is provided to generate a vacuum in the mixing space for mixing said components under vacuum, wherein a mixing means is provided to permit mixing of said first and second components with each other in the mixing space, wherein a discharge means is provided to permit discharge of mixed bone cement from the mixing space, wherein an outer container and the mixing member are designed as two separate members, wherein the sealed container with the second component is provided in the outer container, wherein a coupling device is provided for connecting the outer container and the mixing member to each other and wherein the sealed container can be opened when it is provided in the outer container to permit flow of the second component to the first component in the mixing space for mixing of said components.

BRIEF DESCRIPTION OF THE DRAWINGS

The invention will be further described below with reference to the accompanying drawings, in which

FIG. 5 is another sectional view of the mixing device of FIG. 4; and

FIG. 6 is an alternative detailed view in section of a valve device in the mixing device of FIG. 4.

DESCRIPTION OF THE INVENTION

Figure 1:
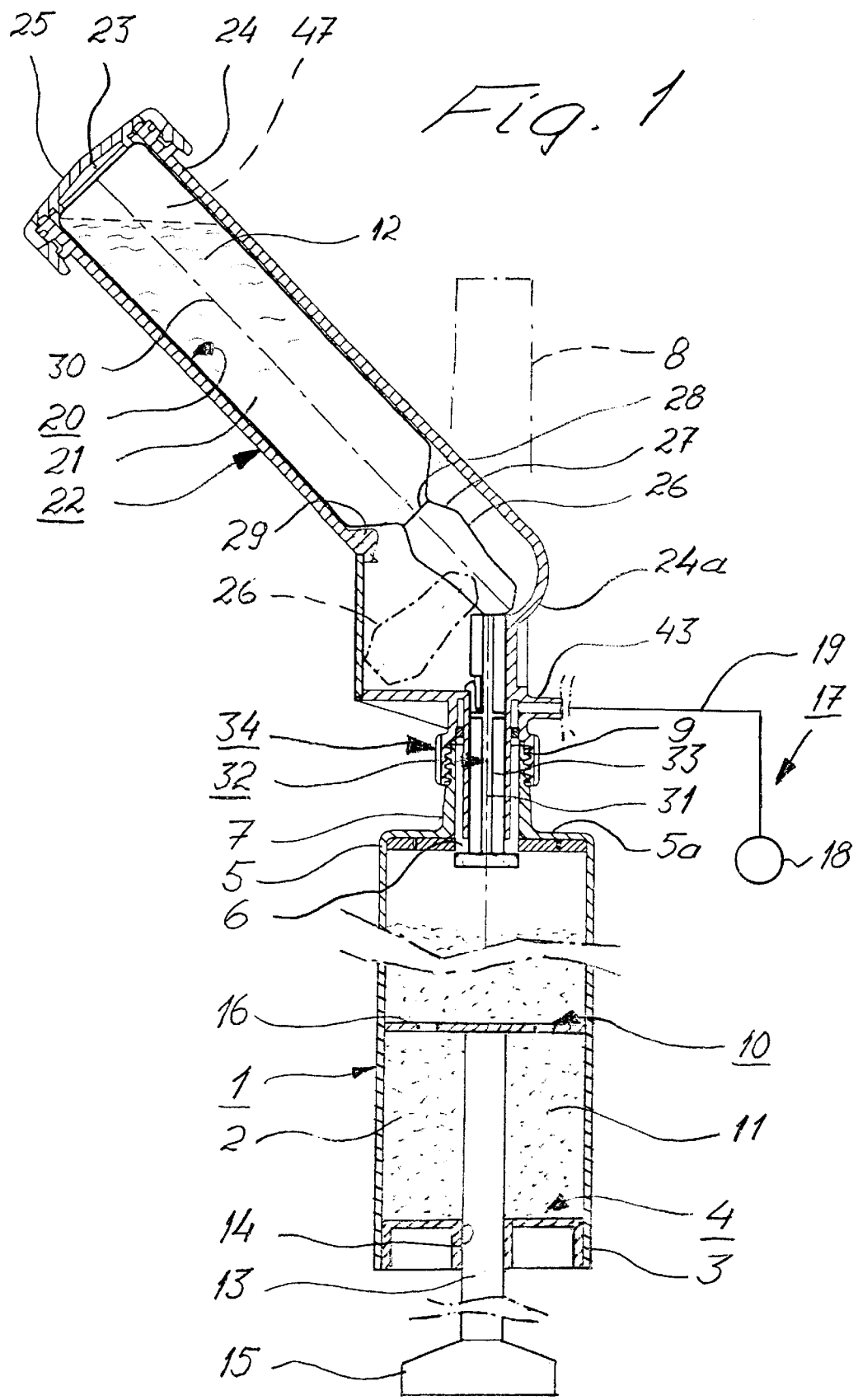
FIG. 1 is a partly sectional view of the mixing device according to the invention.

The mixing device illustrated in the drawings is intended for mixing bone cement under a vacuum and by means of a mixing means. The illustrated mixing device is also intended to permit use of an outer container for existing monomer containers at one and same mixing member and thus, need not manufacture a special type of monomer container for said mixing member.

To this end, the mixing device illustrated in FIG. 1 comprises a mixing member 1 which e.g. has a cylindrical shape and which defines a mixing space 2 for mixing bone cement. The mixing member 1 has a first end portion 3 with a discharge means 4 and a second end portion 5 with a discharge opening 6 for discharge of ready mixed bone cement from the mixing space 2. At the second end portion 5, the mixing member 1 has an end side 5a which is integral with a cylindrical part of the mixing member 1 or which is fastened with screws or in another way secured to the cylindrical part. The discharge means 4 may in a manner known per se be fixedly connected to the first end portion 3. When the bone cement has been mixed, the discharge means 4 is released and then displaced inwards into the mixing space 2 by means of a press device, e.g. a press gun of prior art type, such that bone cement is fed out of the mixing space 2 through the discharge opening 6, a projecting part, preferably a tubular member 7 and a discharge pipe 8 (indicated by dashed and dotted lines in FIG. 1) mounted thereon. The tubular member 7 is fixedly attached to the end side 5a at the second end portion 5 of the mixing member 1 and has external threads 9. The discharge pipe 8 has internal threads (not shown) matching the external threads 9 on the tubular member 7, whereby the discharge pipe 8, when necessary, can be screwed onto said tubular member 7 and unscrewed therefrom. The tubular member 7 protrudes, in the illustrated embodiment, in an axial direction from the second end portion 5 of the mixing member 1.

The mixing device further comprises a mixing means 10 for mixing, in the mixing space 2, a first component 11, preferably a pulverulent polymer, and a second component 12, preferably a liquid monomer, with each other. The mixing means 10 includes a rod 13 which through an opening 14 in the discharge means 4 extends into the mixing space 2. The rod 13 is outside the mixing space 2 provided with a handle 15 which is adapted to facilitate operation of the mixing means 10. The rod 13 further comprises, inside the mixing space 2, a perforated mixing portion 16 which is formed such that it permits effective mixing of said components 11, 12. The rod 13 is displaceably as well as rotatably mounted in the discharge means 4 and it has such a length that the mixing means 10 can be brought all the way to the second end portion 5 of the mixing member 1.

A vacuum-generating device 17 comprises a pump aggregate 18 or similar and a coupling hose 19 or similar and is adapted to generate a suitable vacuum in the mixing space 2 during mixing therein of the bone cement. Vacuum-generating devices for this purpose are wellknown and so is the principle to mix bone cement under a vacuum and the advantages obtained thereby.

The second component 12 is packed up in a sealed container 20 which in the illustrated embodiment is a glass ampoule or vial 21, but which instead can be a container of another type, e.g. a plastic container such as a plastic bag. The glass ampoule or vial 21 can be located in a separate outer container 22 by insertion thereof into said outer container through an opening 23 in a rear end portion 24. Said opening 23 can be air-tightly sealed by means of a cover 25. The glass ampoule or vial has a tip 26 which is secured through a narrow neck 27 which may have a kerf or fractural impression 28 consisting of a thin-walled portion. The glass vial 21 is supported by a support portion 29 in the outer container 22. The outer container 22 holds the glass vial 21 in such a position that the angle a between a longitudinal centre line 30 along the glass vial 21 and a longitudinal centre line 31 along an opening means 33 in an opening device 32 is between e.g. 110–160°, preferably about 135°.

The outer container 22 has a protruding part, preferably a tubular member 35 which together with the tubular member 7 of the mixing member 1 defines a coupling device 34 for connecting the outer container 22 and the mixing member 1 to each other. The tubular member 35 of the outer container 22 has internal threads 36 matching into the external threads 9 of the tubular member 7, whereby the outer container 22 and the mixing member 1 can be secured to each other as shown in FIG. 1. Said tubular member 35 is provided on a front end portion 24a of the outer container.

Figure 2:
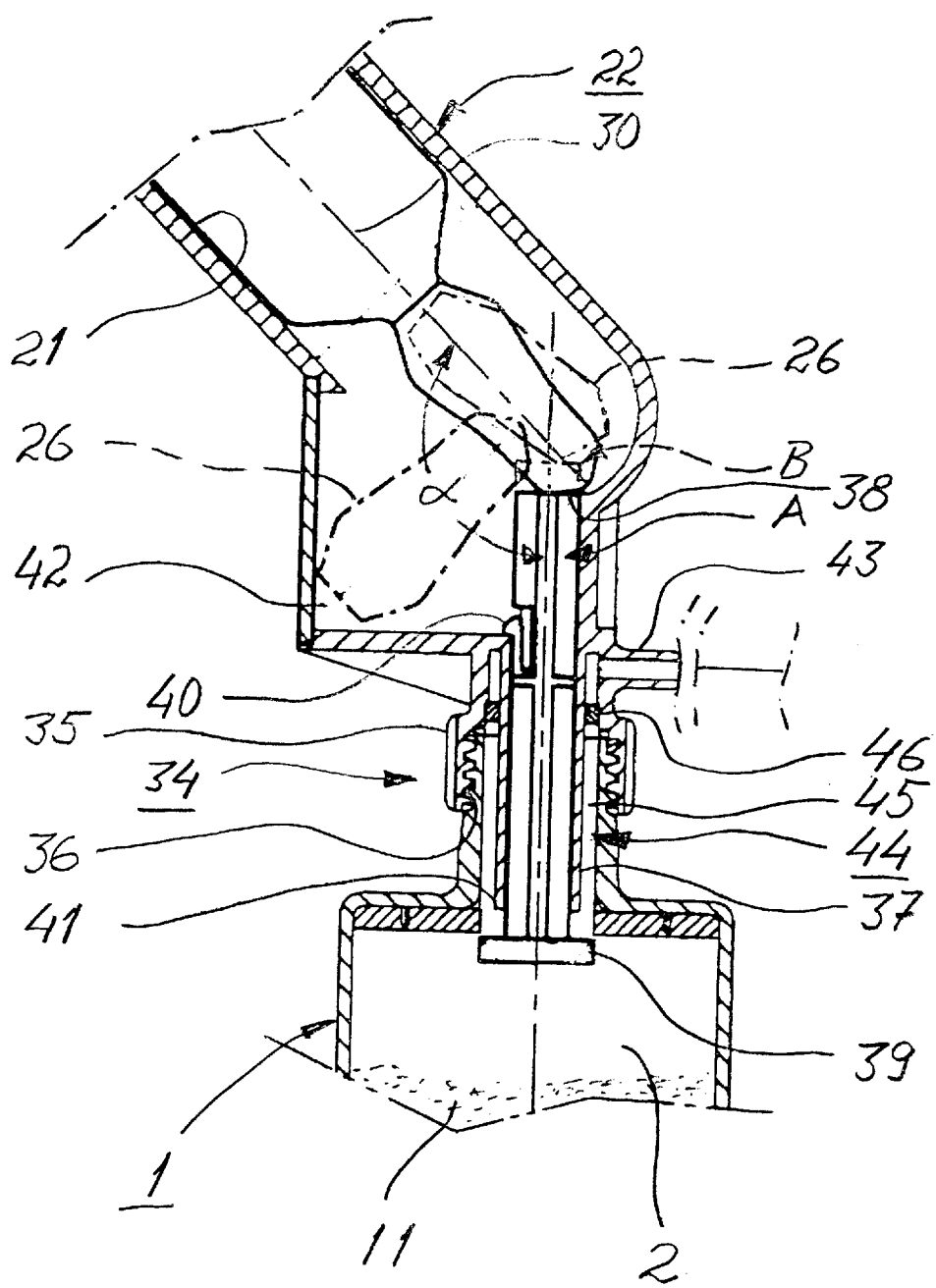
FIG. 2 is an enlarged view of a part of the mixing device of FIG. 1.

The outer container 22 has a double-ended open pipe 37 which is mounted inside the tubular member 35 and extends a short distance out of said member 35. The opening means 33 of the opening device 32 is mounted displaceable in axial direction inside this pipe 37, whereby said pipe 37 controls the opening means 33. The opening means 33 is preferably provided in the pipe 37 and/or designed such that the second component 12 may pass through the pipe 37 from the outer container 22 to the mixing space 2. When the opening means 33 is situated in a rest position A (illustrated with unbroken lines in FIG. 2), an inner end portion 38 thereof is located within the pipe 37 and in level with the tip 26 of the glass ampoule or vial 21. An outer end portion 39 of the opening means 33 is located outside the pipe 37 and inside the mixing space 2 when the outer container 22 and the mixing member 1 are connected to each other. The opening means 33 has a hook member 40 which prevents it from sliding out of the pipe 37 and the outer end portion 39 is designed such that it engages an end edge 41 of the pipe 37 so that said opening means 33 can not be moved further into the outer container 22 than to an opening position B (shown with dashed and dotted lines in FIG. 2), whereby said opening means 33 breaks the tip 26 along the kerf or fractural impression 28. This displacement of the opening means 33 is accomplished by means of the mixing means 10, the rod 13 of which has such a length that it can be moved all the way to the opening means 33 for displacement thereof to the opening position B.

The outer container 22 preferably comprises a space 42 for the tip 26 of the glass ampoule or vial 21. This space 42 is provided and designed such that the broken tip 26 falls down into said space with its open end directed downwards (see dashed and dotted position of the tip 26 in FIG. 1). Hereby, the tip 26 is emptied on its content, i.e. amounts of the second component 12 present therein can flow through the pipe 37 to the mixing space 2.

The outer container 22 also comprises a coupling member 43, e.g. a pipe piece, for connection of the vacuum-generating device 17 and preferably of the coupling hose 19. This coupling member 43 communicates with the mixing space 2 of the mixing member 1 through a communicating member 44. At the embodiment shown, the pipe 37 defines the communicating member 44 while said pipe 37 between the outer side thereof and the tubular member 7 defines a communicating passage 45 which runs from the interior of the coupling member 43 to the interior of the mixing space 2. Since the second component 12 flows, through the interior of the pipe 37, from the outer container 22 into the mixing space 2, the pipe 37 will also separate the communicating passage 45 from the second component 12 when said second component flows to the mixing space 2, i.e. the pipe 37 will prevent or at least obstruct suction of the second component 12 into the vacuum-generating device 17 when this is operative. In order to further ensure that neither the second component 12 nor the first component 11 is sucked into the vacuum-generating device 17, a filter device 46 may be provided in the communicating passage 45.

The outer container 22 is preferably designed such that it accomodates different types of existing sealed containers 20 with the second component.

The coupling member 43 is preferably located on inner parts of the tubular member 35, e.g. just opposite the space 42.

The mixing device illustrated in FIG. 1 operates such that the glass ampoule or vial 21 or a corresponding sealed container with the second component 12 is placed in the outer container 22. Then, the outer container 22 is sealed by means of the cover 25, whereupon said outer container and the mixing member 1 are connected to each other—which at the illustrated embodiment is done by screwing them together such that they are tightly secured to each other. Thereafter, the coupling member 43 of the outer container 22 is connected to the vacuum-generating device 17 or vice versa. Then, the vacuum-generating device 17 is activated, whereby a negative pressure is generated in the mixing space 2 as well as in inner portions of the outer container 22. In the next moment, the opening means 33 is by means of the mixing means 10 brought in a direction towards the tip 26 of the glass ampoule or vial 21 until said tip 26 is broken off along the kerf or fractural impression 28, whereupon said tip 26 falls down into the space 42 and is emptied therein. Since the tip 26 has been broken off the glass vial 21, the second component 12 is emptied or poured out therefrom and flows through the pipe 37 into the mixing space 2, i.e. to the first component 11 provided therein. The portion or amount of the second component 12 emptied from the tip 26 also flows to the mixing space 2.

Emptying of the glass ampoule or vial 21 is facilitated by the provision of an air pad 47 at atmospheric pressure therein and in order to prevent glass shutter from reaching the mixing space 2, a filter (not shown) may be provided in a suitable manner and/or the opening means 33 may be designed in an appropriate manner for this purpose.

In a subsequent moment or step, mixing of the first and second components 11, 12 is carried through in the mixing space 2 under a vacuum and by means of the mixing means 10. When the bone cement is ready, the mixing means 10 can be pulled outwards as far as possible and then broken off close to the discharge means 4. Then, the discharge means 4 is released, whereby the bone cement is collected under vacuum in the space adjacent the tubular member 7, since the discharge means 4 is sucked into the mixing space 2. Finally, the mixing member 1 is placed in said press device and by means thereof, the discharge means 4 is displaced in a direction towards the discharge pipe 8, which means that the bone cement is fed out of or discharged from the mixing device.

Figure 3:
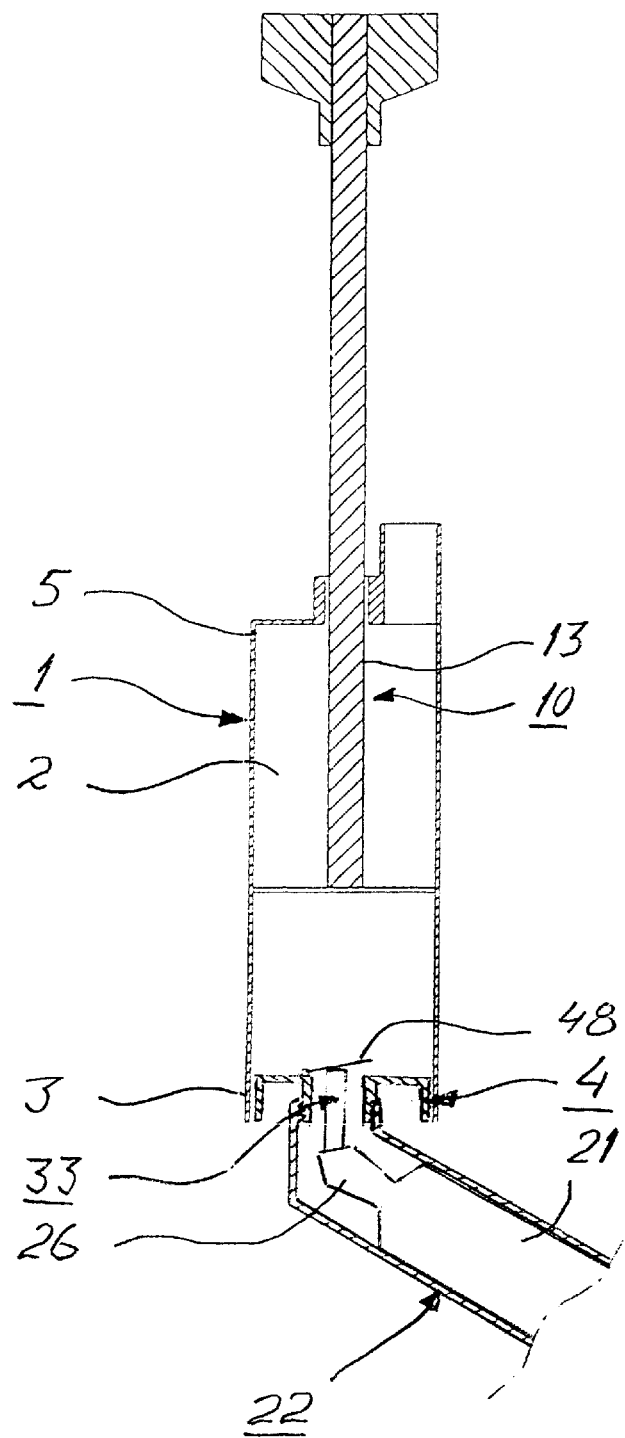
FIG. 3 is a partly sectional view of an alternative embodiment of the mixing device according to the invention.

However, the mixing device is not limited to the embodiment described above, but may vary within the scope of the subsequent claims. Thus, FIG. 3 illustrates that the outer container 22 and the mixing member 1 can be connected to each other in other ways, namely e.g. by connecting the outer container 22 and the discharge means 4 of the mixing member 1 to each other in a suitable manner. At this embodiment, schematically illustrated in FIG. 3, the mixing means 10 is provided on the opposite end portion of the mixing member 1 and it can cooperate with an opening means 33 which is located adjacent the discharge means 4. There may be a flap or cover 48 or similar in the discharge means 4 through which the mixing means affects the opening means 33. This flap or cover 48 is open for admitting the second component 12 into the mixing space 2, but it is closed during discharge of bone cement from the mixing space 2.

As other alternative embodiments of the mixing device it should be mentioned that the sealed container 20 may be of any suitable material, that there may be room for more than one sealed container 20 in the outer container 22, that the coupling device 34 may be of another type than shown, that the outer container 22 may be designed in other ways than shown and that the opening device 32 also may be designed in other ways than shown. The opening device 32 is in such case adapted for opening the sealed containers 20 of different types and/or different numbers of sealed containers 20.

The coupling device 34 may also be designed such that separate, differently sized outer containers 22 for sealed containers of different sizes and the mixing member 1 can be connected to each other. The coupling member 34 may also be designed to permit that outer containers 22 for one sealed container 20 and outer containers 22 for several sealed containers 20 and the mixing member 1 can be connected to each other. Hereby, it will be possible to empty differently sized and/or one or more sealed containers 20 in one and same mixing member 1. It is also possible to design the protruding members 7, 35 in other ways than tubular and/or to attach or secure these to each other in other ways than by screwing them together. If the outer container 22 contains a sealed container 20 which can be opened in one way, several sealed containers 20 located in the outer container 22 may be opened in the same way, e.g. by means of the opening device 32.

The mixing space 2 of the mixing member 1 may include the first component 11 at delivery and the mixing space 2 is in such case sealed. Alternatively, the mixing space 2 may be empty at delivery and be provided with the first component 11 first when mixing is to be carried through.

As an alternative to the described opening device 32, it should be mentioned that said opening device may be defined in that the outer container 22 can be connectable to the mixing member 1 such that its position may be altered relative to the mixing member 1 and/or the outer container 22 may be made of such deformable material that the sealed container 20 can be opened by changing the position and/or the shape of the outer container 22.

As is apparent from the description, the mixing member 1 lacks space for the outer container 22 and the coupling device 34 instead permits location of said outer container outside the mixing member 1. Hereby, different existing monomer containers 20 can be used and placed in the outer container 22, which thus, need not be designed to fit into any space in the mixing member 1. That the outer container 22 is located outside a space in the mixing member 1 also means that the mixing member 1 can be given a simple design and be made small and easy to handle.

It should further be mentioned that the outer container 22 may consist of transparent material such that one can see into the container and that the coupling member 43 for connection of the pump aggregate 18 for generating a vacuum in the mixing space 2, can be located in another place than on the outer container 22.

Figure 4:
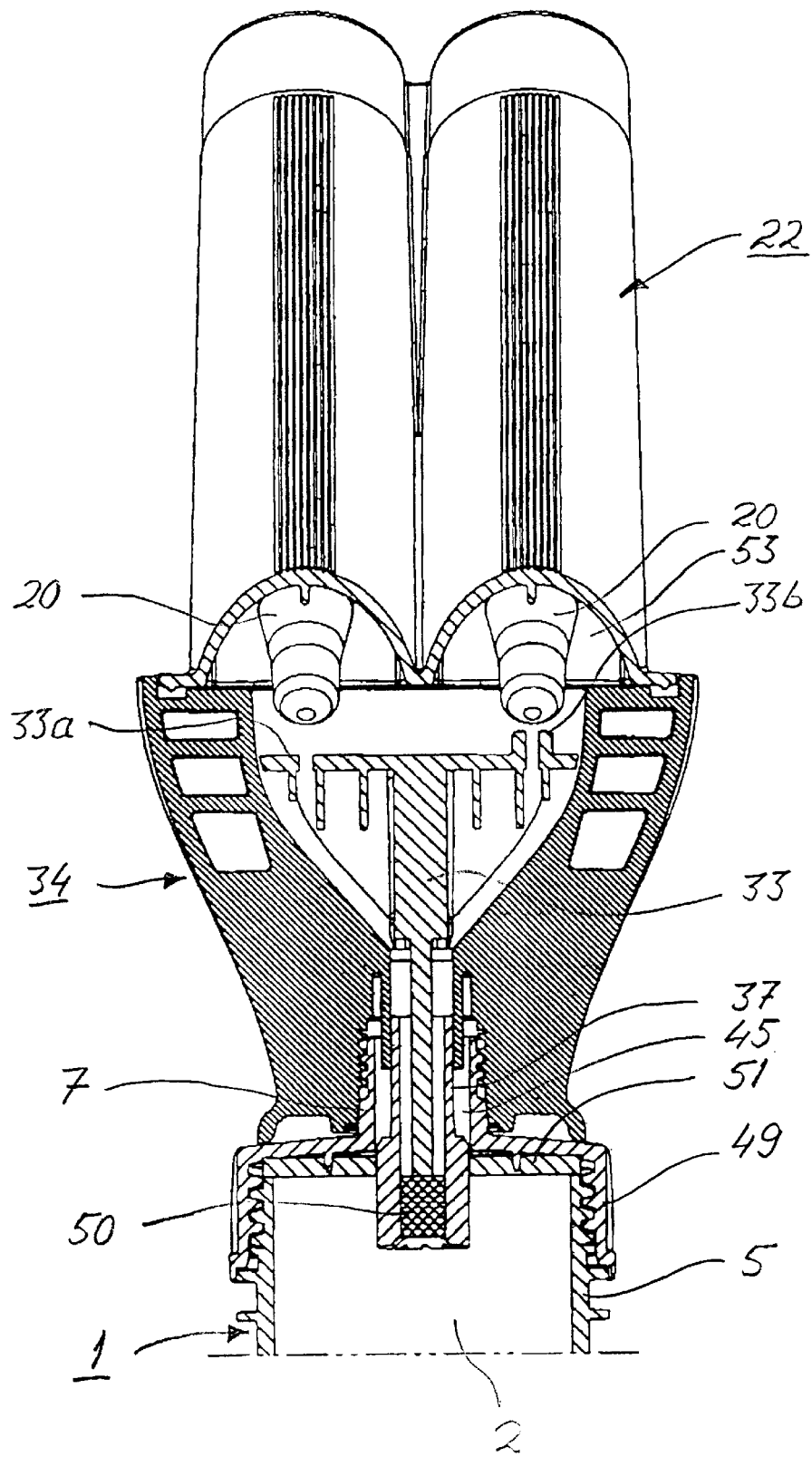
FIG. 4 is a sectional view of another alternative embodiment of the mixing device according to the invention.

At the embodiment of FIGS. 4 and 5, the mixing member 1 is at its opposite end portion 5 provided with a cover or cap 49 which is screwed onto said end portion 5. This cover 49 includes the tubular member 7 which forms a part of the coupling device 34 and on which the discharge pipe 8 can be screwed when the bone cement is mixed and ready for discharge from the mixing space 2. The pipe 37 may down below have a filter device 50 for preventing glass shutter or similar from the glass ampoule or vial 21 or similar to reach the mixing space 2.

Immediately within the cover 49, in the mixing space 2, there may be provided a filter device 51 through which the gases pass from the mixing space 2 to the vacuum-generating device 17 for preventing the components 11, 12 from being sucked into said device 17.

The outer container 22 is at said latter embodiment, through a pivot device 52 at its front portions, pivotally provided on the tubular member 35 of the coupling device 34 such that it can be moved or lowered into a position in which a front opening 53 therein is opened for insertion from the front of the sealed container 20 through said opening 53. When the sealed container 20 is in position in the outer container 22, said outer container can once again be moved or let in and locked in position by means of a snap-in device 54.

The outer container 22 may contain one or more sealed containers 22, e.g. two sealed containers 20 as is shown in FIG. 4. At one embodiment of the outer container 22 with e.g. two sealed containers 20, the opening means 33 may have two opening members 33a, 33b which are step-wise displaced or offset relative to each other such that the opening means 33 first opens one of the sealed containers 20 and then the other.

As is apparent from FIG. 6, the filter device 51 may be provided in the mixing space 2 at some distance from the cover 49—or from the corresponding end side 5a such that gases can flow from the mixing space 2, in axial direction R relative thereto, through the filter device 51 to the communicating passage 45. The filter device 51 may be retained in this position by means of ribs 55 on the cover 49 or the corresponding end side 5a.

The invention is not limited to the embodiments described above and illustrated in the drawings, but may vary within the scope of the subsequent claims. As examples of alternatives not shown, it can be noted that the outer container 22 may be movable, e.g. rotatable relative to an opening means (not shown) such that the sealed container 20 therein is opened when it is brought in contact with the opening means.

Having described the invention, the following is claimed:

1. Mixing device for the manufacture of bone cement by mixing components intended therefor, said mixing device including a mixing member (1) with a mixing space (2) for mixing of said components (11, 12), wherein the components (11, 12) are provided separated from each other before mixing thereof in the mixing device, wherein a first component (11) for the manufacture of bone cement is provided in the mixing space (2) in which mixing is to be carried through, wherein a second component (12) for the manufacture of bone cement is provided in at least one sealed container (20), wherein an opening device (32) is provided for opening the sealed container (20), wherein a vacuum-generating device (17) is provided to generate a vacuum in the mixing space (2) for mixing said components (11, 12) under vacuum, wherein a mixing means (10) is provided for mixing said first and second components (11, 12) with each other in the mixing space (2), wherein a discharge means (4) is provided to permit discharge of mixed bone cement from the mixing space (2), wherein the sealed container (20) with the second component (12) is provided in an outer container (22), wherein a coupling device (34) is provided for connecting the outer container (22) and the mixing member (1) to each other, and wherein the sealed container (20) can be opened when it is provided in the outer container (22) to permit flow of the second component (12) to the first component (11) in the mixing space (2) for mixing of said components (11, 12), characterized in that the outer container (22) and an end portion (5 or 3) of the mixing member (1) can be connected to each other and that the mixing means (10) is movably mounted relative to the mixing space (2) at an opposite end portion (3 or 5) of the mixing member (1).

2. Mixing device according to claim 1, characterized in that the opening device (32) can be directly or indirectly affected by the mixing means (10) to open the sealed container (20) inside the outer container (22).

3. Mixing device according to claim 2, characterized in that the mixing means (10) includes a rod (13) which from the outside extends into the mixing space (2) through an opening (14) in the discharge means (4) and that the rod (13) is sealingly and movably mounted in the discharge means (4).

4. Mixing device according to claim 3 characterized in that the rod (13) has such length that it permits the mixing means (10) to displace the opening means (33) for opening of the sealed container (20).

5. Mixing device according to claim 1, characterized in that the opening device (32) comprises an opening means (33) which is movably mounted between the mixing means (10) and the sealed container (20) inside the outer container

(22) and that the opening means (33) is maneouvrable by means of the mixing means (10) for opening the sealed container (20).

6. Mixing device according to claim 5, characterized in that the opening means (33) of the opening device (32) is movably mounted on the outer container (22).

7. Mixing device according to claim 6, characterized in that the opening means (33) extends through such a protruding member (35) of the outer container (22) which forms part of the coupling device (34).

8. Mixing device according to claim 7, characterized in that the opening means (33) extends into the outer container (22) and out beyond the protruding member (35) of said outer container (22) as well as into a protruding member (7) which is provided on the mixing member (1) and which forms part of the coupling device (34).

9. Mixing device according to claim 1, characterized in that the mixing member (1) has no space for the outer container (22) and that the coupling device (34) permits connection of the outer container (22) to the mixing member (1) such that said outer container is located outside said mixing member (1).

10. Mixing device according to claim 9, characterized in that the mixing member (1) further lacks space for the coupling device (34) and that said coupling device (34) is also located outside said mixing member (1).

11. Mixing device according to claim 9, characterized in that the mixing member (1) defines only one substantial space, namely the mixing space (2).

12. Mixing device according to claim 1, characterized in that the coupling device (34) is designed to permit the second component (12) to flow, through said coupling device (34), after opening of the sealed container (20), from said sealed container (20) into the mixing space (2) and the first component (11) provided therein.

13. Mixing device according to claim 1, characterized in that the coupling device (34) comprises a member (7) which protrudes from one end portion (5 or 3) of the mixing member (1) and another member (35) which protrudes from an end portion (24a) of the outer container (22), said protruding members (7, 35) being connectable to each other.

14. Mixing device according to claim 13, characterized in that the member of the coupling device (34) protruding from the mixing member (1) is a tubular member (7) which is fixedly attached to an end side (5a) of the mixing member (1) and which protrudes in axial direction relative to the mixing member (1), that the member of the coupling device (34) protruding from the outer container (22) is a tubular member (35) and that the tubular members (7, 35) of the coupling device (34) can be sealingly connected to each other.

15. Mixing device according to claim 14, characterized in that the tubular members (7, 35) have threads (9, 36) which are designed to permit screwing together of said tubular members (7, 35).

16. Mixing device according to claim 14, characterized in that the tubular member (7) on the mixing member (1) is a member which permits connection of a discharge pipe (8) through which ready mixed bone cement is discharged from the mixing space (2).

17. Mixing device according to claim 1, characterized in that the outer container (22) is sealed, that the outer container (22) and the mixing member (1) are closely connected to each other through the coupling device (34) and that the inner portions of the outer container (22) communicate with the mixing space (2) so that the vacuum-generating device (17) generates a vacuum in the mixing space (2) as well as in the inner portions of the outer container (22).

18. Mixing device according to claim 1, characterized in that the outer container (22) includes a coupling member (43) for connection of the vacuum-generating device (17) and that the coupling member (43) through a communicating member (44) communicates with the mixing space (2) of the mixing member (1) when the outer container (22) and the mixing member (1) are connected to each other.

19. Mixing device according to claim 18, characterized in that the communicating member (44) is separated from such a member through which the second component (12) flows from the outer container (22) to the mixing space (2).

20. Mixing device according to claim 18, characterized in that a pipe (37) is provided to separate the communicating member (44) from said member through which the second component (12) flows from the outer container (22) to the mixing space (2).

21. Mixing device according to claim 1, characterized in that the outer container (22) and the mixing member (1) are connected to each other while mixing of bone cement is carried through under a vacuum in the mixing space (2) by means of the mixing means (10).

22. Mixing device according to claim 1, characterized in that the outer container (22) is removable from the mixing member (1) when mixing of the bone cement in the mixing space (2) has been terminated such that other members can be connected to the end portion (5) of the mixing device (1) to which the outer container (22) has been connected.

23. Mixing device according to claim 1, characterized in that the sealed container (20) is a glass ampoule or vial (21).

24. Mixing device according to claim 23, characterized in that the outer container (22) defines a space (42) for receiving a tip (26) which has been broken off from the glass ampoule or vial (21), whereby the broken-off tip (26) is situated in a position in said space (42) such that the second component (12) can flow out of said tip (26).

25. Mixing device according to claim 23, characterized in that the outer container (22) holds the glass ampoule or vial (21) oriented such that the angle ($\alpha$) between a longitudinal centre line (30) along the glass ampoule or vial (21) and its tip (26) and a longitudinal centre line (31) along the opening means (33) is between 110° and 160°.

26. Mixing device according to claim 1, characterized in that an end portion of the mixing member (1) includes a removable cover (49) and that this cover (49) has a tubular member (7) to which a tubular member (35) of a coupling device (34) for connection of the outer container (22) to the mixing member (1) as well as a discharge pipe (8) are attachable.

27. Mixing device according to claim 1, characterized in that, at an end portion (5) of the mixing member (1), a filter device (51) is provided in the mixing space (2) for preventing components (11, 12) from being sucked into the vacuum-generating device (17) from said mixing space (2) and that said filter device (51) is provided such that gases pass therethrough in an axial direction (R) relative to the mixing space (2).

28. Mixing device according to claim 1, characterized in that the outer container (22) has at least one front opening (53), that the front portion of the outer container (22) through a pivot device (52) is pivotally connected to a tubular member (35) of a coupling device (34) through which the outer container (22) can be connected to the mixing member (1), that the outer container (22) can be moved by means of said pivot device (52) such that the sealed container (20) may be inserted through said front opening (53) and that the outer container (22) is there-after. movable towards said tubular member (35) and can be snapped-in onto said tubular member (35).

29. Mixing device according to claim 1, characterized in that the outer container (22) and a discharge means (4) forming part of the mixing member (1) and provided at an end portion (3) thereof, are connected to each other and that the mixing means (10) is movably mounted relative to the mixing space (2) at an opposite end portion (5) of the mixing member (1).

30. Mixing device according to claim 29, characterized in that all sealed containers (20) located in the outer container (22) can be opened with the same opening device (32).

31. Mixing device according to claim 1, characterized in that the outer container (22) is designed to contain more than one sealed container (20).

32. Mixing device according to claim 1, characterized in that the coupling device (34) is designed such that outer containers (22) with one size for small sealed containers (20) or another size for larger sealed containers (20) and/or outer containers (22) with one size for a sealed container (20) or another size for several sealed containers (20) are connectable to each other, whereby differently sized and/or a different number of sealed containers (20) can be emptied in one and same mixing member (1).

33. Mixing device according to claim 1, characterized in that the outer container (22) consists of such transparent material that one can see thereinto.

34. Mixing device according to claim 1, characterized in that the mixing space (2) of the mixing member (1) is sealed and contains the first component (11) and that the mixing space (2) can be opened before the mixing member (1) and the outer container (22) are connected to each other.

35. Mixing device according to claim 1, characterized in that the mixing space (2) of the mixing member (1) is empty and is provided with the first component (11) first when mixing is to be carried through.

36. Mixing device according to claim 1, characterized in that the outer container (22) is designed to receive different types of existing sealed containers (20) with the first component (11).

37. Mixing device according to claim 1, characterized in that the outer container (22) is movably mounted relative to an opening means which permits opening of the sealed container (20) when said sealed container (20) is brought in contact with said opening means.

* * * * *